US005965789A

United States Patent [19]
Lubon et al.

[11] Patent Number: 5,965,789
[45] Date of Patent: Oct. 12, 1999

[54] ENGINEERING PROTEIN POSTTRANSLATIONAL MODIFICATION BY PACE/FURIN IN TRANSGENIC NON-HUMAN MAMMALS

[75] Inventors: Henryk Lubon, Rockville, Md.; William N. Drohan, Springfield, Va.; Rekha K. Paleyanda, Gaithersburg, Md.

[73] Assignee: American Red Cross, Washington, D.C.

[21] Appl. No.: 08/434,834

[22] Filed: May 4, 1995

Related U.S. Application Data

[63] Continuation-in-part of application No. 08/247,484, May 23, 1994, Pat. No. 5,589,604, and a continuation of application No. 08/198,068, Feb. 8, 1994, abandoned, said application No. 08/247,484, is a continuation of application No. 07/638,995, Jan. 11, 1991, abandoned, which is a continuation-in-part of application No. 07/943,246, Sep. 10, 1992, Pat. No. 5,831,141.

[51] Int. Cl.[6] .................. A01K 67/00; A01K 67/027; C12P 21/04; C12P 21/06
[52] U.S. Cl. .................. 800/14; 800/7; 435/69.1; 435/69.6
[58] Field of Search ................ 800/2, 7, 14; 536/23.1, 536/24.1; 435/320.1, 240.2, 172.3, 69.1, 69.6

[56] References Cited

U.S. PATENT DOCUMENTS

| | | | |
|---|---|---|---|
| 4,775,624 | 10/1988 | Bang et al. | 435/226 |
| 4,873,316 | 10/1989 | Meade et al. | 530/412 |
| 4,959,318 | 9/1990 | Forster et al. | |
| 4,968,626 | 11/1990 | Forster et al. | |
| 4,992,373 | 2/1991 | Bang et al. | 435/69.6 |
| 5,667,839 | 9/1997 | Berg | 426/657 |

FOREIGN PATENT DOCUMENTS

| | | |
|---|---|---|
| 0 264 166 | 4/1988 | European Pat. Off. |
| 0 279 582 | 8/1988 | European Pat. Off. |
| 319 944 | 6/1989 | European Pat. Off. |
| WO 88/00239 | 1/1988 | WIPO |
| WO 88/01648 | 3/1988 | WIPO |
| WO 90/05188 | 5/1990 | WIPO |
| WO92/09698 | 6/1992 | WIPO |

OTHER PUBLICATIONS

Kappel, C. et al (1992). Current Opinion; Biotechnology 3, 548–553.
Colman, A (1996). Am. J. Clin. Nutr. 63, 639S–455.
Strojek, R. et al (1988). Genetic Engineering: Principles and Methods, v. 10, pp. 221–246. Plenum Press.
Low, M. et al (1985). Cell 41, 211–219.
Drews, R. et al (1995). J. of Cellular Biochemistry Suppplement D (19B), 256.
Denman et al. "Transgenic Expression of a Variant of Human tPA in Goat Milk: Purification and Characterization of the Recombinant Enzyme", *Bio/Technology*, vol. 9:839–843, (Sep. 1991).
Ebert et al. "Transgenic Production of a Variant of Human tPA in Goat Milk: Generation of Transgenic Goats and Analysis of Expression", *Bio/Technology*, vol. 9:835–838, (Sep. 1991).
Gordon et al. "Production of Human Tissue Plasminogen Activator in Transgenic Mouse Milk", *Bio/Technology*, vol. 5:1183–1187, (Nov. 1987).
Krimpenfort et al. "Generation of Transgenic Dairy Cattle Uisng 'In Vitro' Embryo Production", *Bio/Technology*, vol. 9:844–847, (Sep. 1991).
Walls et al. "Amplification of Multicistronic Plasmids in the Human 293 Cell Line and Secretion of Correctly Processed Recombinant Human Protein C", *Gene*, vol. 81:139–149, (1989).
Wright et al. "High Level Expression of Active Human Alpha–1–Antitrypsin in the Milk of Transgenic Sheep", *Bio/Technology*, vol. 9:830, (Sep. 1991).
Yan et al. "Characterization and Novel Purification of Recombinant Human Protein C from Three Mammalian Cell Lines", *Bio/Technology*, vol. 8:655–661, (Jul. 1990).
Velander et al., (1990) Abstract presented at the 1990 Annual Meeting (Nov. 11–16, 1990) of the American Institute of Chemical Engineering, "The Expression of Human Protein C in the Milk of Transgenic Mice".
Grinnell et al., (1990) "Native and Modified Recombinant Human Protein C and Related Anticoagulants", Chapter 3, Bruley and Drohan, Eds., Portfolio Co., The Woodlands, Texas.
Wydro, R.M. (1990) "Transgenic Production Of Protein C" in "Protein C and Related Anticoagulants", An International Symposium, Held Feb. 26–27, 1992 in San Diego, Ca.
Grinnell et al., (1987), *Trans.*, "Activated Expression of Fully Gamma Carboxylated Recombinant Protein C . . . ", *Biotechnology*, vol. 5:1189–1192.
Pittius et al., (1988), "A Milk Protein Gene Promoter Directs The Expression of htPA cDNA In The Mammary Gland In Transgenic Mice", *Proced. Natl. Acad. Sci.*, vol. 85:5874–5878.

(List continued on next page.)

*Primary Examiner*—Deborah Crouch
*Attorney, Agent, or Firm*—Foley & Lardner

[57] ABSTRACT

The invention relates to transgenic non-human multicellular organisms that contain polynucleotides for expressing proteins that alter posttranslational modification. In particular, the invention provides multiply-transgenic animals in which a first transgene encodes a first protein, a second transgene encodes a second protein, and expression of the second protein affects the posttranlational modification of the first protein in cells of said organism. Expression in preferred embodiments is in specific cells and the modified protein is secreted into a bodily fluid. The invention provides related methods, proteins and products. An example provides transgenic animals that express human Protein C and the processing protease PACE/furin in mammary glands and secrete both proteins into milk.

27 Claims, 2 Drawing Sheets

OTHER PUBLICATIONS

Hogan et al., (1986), "Manipulating The Mouse Embryo", *Cold Spring Harbor Laboratory*, Cold Spring Harbor, NY, pp. 153–203.

Clark et al., (1987), TIBTECH, vol. 5:20–24.

Buchthal et al., *Biochemistry*, vol. 22;1077, (1983).

Campbell et al., *Nucleic Acids Research*, vol. 12:8686, (1984).

Plutzky et al., *Proc. Nat'l Acid. Sci. U.S.A.*, vol. 83:546.

Suttie, *Thrombosis Research*, vol. 44:129, (1986).

Velander et al., *Proc. Nat'l Acad. Sci., U.S.A.*, vol. 89:12003, (Dec. 1992).

Vermeer et al., *FEBS Letters*, vol. 148:317, (1982).

Yan et al., *TIBS*, vol. 14:264, (1989).

Hennighausen, L., *Protein Expression and Purification*, vol. 1:2, (1990).

Fair et al., *Blood*, vol. 67:64, (1986).

Foster et al., "Endoproteolytic Processing of the Human Protein C Precursor by the Yeast Kex2 Endopeptidase Coexpressed in Mammalian Cells," *Biochemistry* 30: 367–372 (1991).

Wasley et al., "PACE/Furin Can Process the Vitamin K–dependent Pro–factor IX Precursor within the Secretory Pathway," *J. Biol. Chem.* 268: 8458–8465 (Apr. 25, 1993).

Search report for PCT/US96/06121.

mature HPC

ENGINEERING PROTEIN POSTTRANSLATIONAL MODIFICATION BY PACE/FURIN IN TRANSGENIC NON-HUMAN MAMMALS

This application is a continuation-in-part of application U.S. Ser. No. 08/247,484, now U.S. Pat. No. 5,589,604 filed May 23, 1994 which is a file wrapper continuation application of Ser. No. 07/638,995, filed Jan. 11, 1991, now abandoned, which is a continuation-in-part of Ser. No. 07/943,246 filed Sep. 10, 1992 which is now U.S. Pat. No. 5,831,141 and it is a continuation of U.S. Ser. No. 08/198,068, filed Feb. 8, 1994, now abandoned which are herein incorporated by reference in their entirety.

The present invention relates to transgenic non-human multicellular organisms having cells of altered capacity for posttranslational modification. The invention relates to the transgenic organisms, methods for producing the organisms and substances produced by the organisms. One aspect of the invention particularly relates to optimizing transgenic production of a substance by altering the protein posttranslational modification capacity of cells in a transgenic organism. In another aspect, the invention relates particularly to substances produced by transgenic animals having altered capacities for posttranslational modification. In yet another aspect, the invention relates particularly to altering the constitution of a physiological compartment, tissue organ or body fluid in a transgenic organism by altering posttranslational protein modification in cells of the organism. In this regard the invention also relates to cells, cellular products, tissues, organs and fluids modified by altering the posttranslational protein modification of cells in the transgenic organism. In a preferred aspect, the invention specifically relates to improved maturation of proteolytically processed proteins by expressing a processing protease in cells of a transgenic organism. In this aspect, the invention relates especially to expression of PACE/furin and, further, to the maturation of precursor proteins involved in blood coagulation and clot dissolution.

BACKGROUND OF THE INVENTION

The expression of cloned or purposefully altered genes in transgenic organisms has been seen to hold great promise for the production of substances by transgenic "bioreactors" and for the production of improved animals and plants, among other applications. Obstacles to realizing the promise have been encountered, however. In particular, it has not been possible to obtain highly efficient production of properly modified useful substances in transgenic animals. The present invention relates to methods and transgenic organisms that overcome the problem and to products produced by the transgenic organisms, inter alia.

Many DNAs have been cloned and expressed in cells in culture to produce heterologous proteins, peptides and other substances. Several genes also have been introduced into plants or animals to produce heterologous proteins, peptides and other substances. Although it has been possible, in general, to engender expression and production of proteins and other substances in cells, animals and plants by expressing cloned genes, the production levels that have been obtained often have been low and the posttranslational processing of proteins produced this way generally has been incomplete or inefficient. These difficulties particularly have limited, or precluded, the use of animal and plant bioreactors to produce proteins with the proper posttranslational modifications. Low production levels and low specific activities in cultured cells have been attributed to the expression of limiting amounts of particular enzymes necessary for the production of the expressed protein in its properly modified form.

Attempts have been made to increase production of properly modified proteins in cells in culture by expressing a cloned gene to increase the amount of a limiting enzyme activity in the cells. For instance, expression of a transfected yeast Kex2 cDNA in baby hamster kidney ("BHK") cells that expressed human Protein C ("HPC") from an amplified Protein C gene increased the conversion of Protein C from the single-chain zymogen form to the mature two-chain form (Foster et al., Biochemistry 30: 367–372 (1991)).

In another example, PACE/furin expressed at high levels by a transfected DNA in chinese hamster ovary cells ("CHO") apparently increased proper cleavage of the propeptide of the co-expressed Factor IX precursor (Wasley et al., J. Biol. Chem. 268: 8458–8465 (1993)).

But, the processing activity apparently engendered by expression of the PACE/furin gene in these experiments was difficult to discern and varied. In addition, apparent increases in protease activity seemed to cause cell toxicity, cytopathic effect and alterations in markers of cellular differentiation. Indeed, it has been suggested that PACE/furin and similar processing enzymes may be deleterious or lethal to cells when they are inappropriately expressed, even in culture, as noted for instance by Schalken et al., J. Clin. Invest. 80: 1545–1549 (1987), Ayoubi et al., J. Biol. Chem. 269: 9298–9303 (1994) and Decroly et al., J. Biol. Chem. 269: 12240–12247 (1994). The potential for improving the cellular production of substances in this way is overshadowed by the adverse affects observed in culture.

In light of such results, this approach to improving production of proteins, polypeptides and other substances in transgenic organisms has not been favorably considered. For one, expression of enzymes that alter posttranslational modification in cells thus far has been carried out only in abnormal cultured cells. These cells generally exhibit aberrant growth, which allows them to propagate indefinitely in artificial media. Largely, such cells are derived from tumors or are the outcome of transduction with immortalizing viruses. Differentiation and growth factors particularly are altered in such cells. Thus, the response of these cells to altered posttranslational modification capacity does not indicate the expected response of cells in a healthy organism.

Indeed, it has been thought that such cells are far more tolerant than an intact organism of adverse effects stemming from altered expression of enzymes affecting posttranslational modifications. Given the role of posttranslational modifications in controlling enzyme cascades and in modulating the activity of factors that control growth, mitosis and differentiation, including processes that generally occur only in intact organisms, altering posttranslational modification capacities poses a greater risk of being severely deleterious to an intact organism, even when it would not adversely impact a cell grown in culture.

A developing organism is especially sensitive to inappropriate expression, particularly expression that causes cytopathic effect. For example, loss of a single cell at a critical stage can hopelessly incapacitate or abort a developing embryo.

In addition, an organism can be adversely affected not only by intracellular effects but also by physiological communication of the activity from expressing cells to other parts of the organism. The complex physiological processes involved in transport and metabolism of circulating proteins, moreover, often has the potential to amplify a tolerable intracellular effect into an effect that is intolerably damaging to the organism as a whole.

For instance, it has been noted that expression of some enzymes that carry out posttranslational modifications can activate toxins. Altering a posttranslational modification that activates a toxin thus, potentially could amplify ordinarily tolerable toxin levels, such as those produced by a mild infection, to levels seriously harmful or lethal to an organism (Chiron et al., *J. Biol. Chem.* 269: 18167–18176 (1994)).

A variety of enzymes involved in posttranslational modification of proteins, moreover, are expressed differently in the cells of different tissues in an organism. In addition, expression of such proteins in cells often varies greatly over the course of embryonic development. This is the case, for instance, of the subtilisin-like PACEs, such as PACE/furin, which appear to carry out proteolytic steps in the maturation of some proteins. In fact, it has been suggested that posttranslational modifications, such as the proteolytic cleavages mediated by these processing proteases, not only participate in, but also have a regulatory role in the process of cell differentiation (Zheng et al., *J. Neuroscience*, 14: 4656–4673 (1994). Inappropriate expression of these enzymes in cells of a developing embryo thus could have broadly deleterious or lethal effects.

Concern about deleterious effects in vivo have made it seem unlikely that posttranslational modifications of proteins can be much altered in cells of transgenic organisms. Thus, the idea of changing the posttranslational modification properties of cells has not seemed to be a promising way to improve the ability of transgenic organisms to produce useful substances. Given the potential of such animals for the production of useful substances, it therefore remains an important goal to devise methods that overcome these obstacles to developing efficient bioreactors.

ABBREVIATIONS AND DEFINITIONS

The following abbreviations and terms are used in this application in accordance with their meaning as understood by those of skill in the arts to which the present invention pertains. The following definitions are illustrative and should not be construed to limit the scope of the invention, however.

Abbreviations

B—OH: β-hydroxyl group

BHK: baby hamster kidney cells

CHO: (1) chinese hamster ovary cells; (2) glycoside or sugar moiety, a common protein posttranslational modification ELISA: enzyme-linked immunosorbant assay HC:158–420 heavy chain of human Protein C, containing amino acids 158–420

HPC: human Protein C

HRP: horseradish peroxidase

Gla or GLA: gamma-carboxy glutamic acid, a posttranslational modification of proteins, notable among the vitamin K-dependent proteins involved in blood clotting, clot dissolution, bone, lung.

GPI: glycosylphosphatidylinositol

KR: $Lys^{156}$-$Arg^{157}$ dipeptide released during maturation of human Protein C LC:1–155: light chain of human Protein C, containing amino acids 1 through 155

MAb: monoclonal antibody

PACE: paired basic amino acid cleaving enzyme

PACEM: mutated PACE

PAGE: polyacrylamide gel electrophoresis

PC: prohormone convertase(s)

PCR: polymerase chain reaction

PRO: 24-amino acid propeptide of protein C

SDS: sodium dodecyl sulfate

S—S: disulfide bond

SP: signal peptide t-PA: tissue plasminogen activator

WAP: whey acidic protein rHFIX: recombinant human Factor IX rHPC: recombinant human Protein C Illustrative Definitions MATURATION: The process by which a polypeptide encoded by an mRNA or a region of an mRNA is altered during and after addition of successive amino acid constituents on the ribosome. Ultimately maturation of the polypeptide produces proteins in their physiological forms. Thus, for instance proteolytic events that convert precursor forms to processed forms constitutes maturation. Glycosyl groups also are added during maturation of a protein. Generally, in fact, any posttranslational modification of a protein, as defined herein, affects maturation.

FURIN: One of the prohormone convertases (PCs) or paired basic amino acid cleaving enzymes, referred to herein as PACE/furin.

MULTICELLULAR ORGANISMS: all multicellular animals and plants whose cells become differentiated to form tissues; among animals, the metazoa, which includes all animals except protozoa.

POSTTRANSLATIONAL MODIFICATIONS: Covalent alterations to the 20 naturally occurring amino acids that make up the polypeptide chain(s) of a protein in its unmodified form. Posttranslational modifications occur in the protein backbone and the side chains of the constituent amino acids. Generally, posttranslational modifications are made by formation or breakage of a covalent bond via an enzyme-catalyzed reaction. Some modifications occur before protein synthesis is complete, while others take place after the newly synthesized protein is released from the ribosome. A great variety of posttranslational modifications have been characterized in a diversity of proteins. All such modifications useful in the present invention are encompassed by the use herein of the term "posttranslational modification."

SUMMARY OF THE INVENTION

Therefore, in accordance with one aspect of the invention, there is provided a transgenic non-human multicellular organism comprising cells having incorporated expressibly therein a first polynucleotide that encodes a first protein and a second polynucleotide that encodes a second protein, wherein expression of the second protein affects the posttranslational modification of the first protein in the cells.

In preferred embodiments of this aspect of the invention the transgenic organism is a metazoan animal. In other preferred embodiments it is a plant.

In certain preferred embodiments of this aspect of the invention the polynucleotides and proteins are expressed in specific cells of the organism. In some preferred embodiments the first protein is secreted into a bodily fluid of the organism. Also, in some preferred embodiments the posttranslational modification is required for maturation of the first protein.

In addition, in some preferred particular embodiments the second protein affects a post-translational modification selected from the group consisting of: acetylation, ADP-ribosylation, acylation, ADP-ribosylation, amidation, covalent attachment of a flavin, covalent attachment of a heme, covalent attachment of a nucleotide or a nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer RNA-mediated addition of amino acids to proteins, such as arginylation, and ubiquitination.

In a particularly preferred embodiment the polynucleotides and proteins are expressed in specific cells of the organism and the first protein is secreted into a bodily fluid. Among preferred bodily fluids in this aspect of the invention are blood, milk, urine and saliva.

In another aspect of the invention in this regard in preferred embodiments the first polynucleotide encodes a precursor protein, the second polynucleotide encodes a protease and the precursor protein is processed by the protease, in cells of the organism. In this regard, in certain preferred embodiments, the first protein is a vitamin-K dependent protein or it is Factor VII, Factor VIII, Factor IX, prothrombin, Factor X, Protein C, Factor VII, Protein S, bone Gla protein, matrix Gla protein, growth arrest specific protein 6, antithrombin III, t-PA, erythropoietin, fibrinogen, immunoglobulin or albumin.

In further preferred embodiments of this aspect of the invention the cells are secretory cells of mammary glands and the first protein is secreted into milk of the organism. In this regard, in certain preferred embodiments, the first polynucleotide encodes a precursor protein, the second polynucleotide encodes a protease, and the precursor protein is processed by the protease.

Among preferred particular embodiments of this aspect of the invention, the first protein is Factor VII, Factor VIII, Factor IX, prothrombin, Factor X, Protein C, Factor VII, Protein S, bone Gla protein, matrix Gla protein, growth arrest specific protein 6, antithrombin III, t-PA, erythropoietin, fibrinogen, immunoglobulin or albumin.

In particularly preferred embodiments in this regard the protease is a paired basic amino acid cleaving enzyme. In some especially preferred embodiments in this regard the first polynucleotide encodes Protein C. Among the most particularly preferred in this regard are embodiments in which the protease is PACE/furin.

Among other preferred embodiments in this aspect of the invention are those comprising a third polynucleotide that encodes a third protein that affects protein gamma-carboxylation, wherein the first protein requires gamma-carboxylation for maturation and the third protein affects gamma-carboxylation of the first protein in the cells of the organism. In this regard, embodiment in which the first polynucleotide encodes Protein C and the protease is PACE/furin are especially preferred.

In another aspect, the invention provides a method for producing a posttranslationally modified protein comprising the steps of incorporating expressibly into a transgenic non-human multicellular organism a first polynucleotide that encodes a first protein and a second polynucleotide that encodes a second protein, expressing the first and the second proteins in cells of the organism whereby the second protein affects the post-translational modification of the first protein in the cells, and then isolating the posttranslationally modified first protein from the organism.

Preferred embodiments of this aspect of the invention include those in which the polynucleotides are expressed in specific cells in the organism.

In addition, preferred embodiments include those in which the first protein is secreted into a bodily fluid of the organism. Especially preferred fluids are blood, milk, urine and saliva.

Also preferred are embodiments in which the first polynucleotide encodes a precursor protein, the second polynucleotide encodes a protease and the precursor protein is processed by the protease in the cells.

Among the highly preferred embodiments of this aspect of the invention are those in which the cells are secretory cells of mammary glands and the first protein is secreted into milk of the organism. In this regard, embodiments in which the first polynucleotide encodes a precursor protein, the second polynucleotide encodes a protease, and the precursor protein is processed by the protease in the cells are especially preferred. In some highly preferred embodiments of this type, the first protein is Factor VII, Factor VIII, Factor IX, prothrombin, Factor X, Protein C, Factor VII, Protein S, bone Gla protein, matrix Gla protein, growth arrest specific protein 6, antithrombin III, t-PA, erythropoietin, fibrinogen, immunoglobulin or albumin. In additional, in particularly preferred embodiments of this aspect of the invention the protease is a paired basic amino acid cleaving enzyme. Very highly preferred in this regard are embodiments in which the first polynucleotide encodes Protein C. Also highly preferred are embodiments in which the protease is PACE/furin. Particularly highly preferred are embodiments in which the first polynucleotide encodes Protein C and the protease is PACE/furin.

Additional preferred embodiments of this aspect of the invention include those in which a third polynucleotide encodes a third protein which affects protein gamma-carboxylation, wherein the first protein requires gamma-carboxylation for maturation and the third protein affects gamma-carboxylation of the first protein in cells of the organism. Especially preferred in this regard are those embodiments in which the first polynucleotide encodes Protein C and the protease is PACE/furin.

In yet another aspect, the invention provides a posttranslationally modified protein made by a process comprising the steps of incorporating expressibly into a transgenic non-human multicellular organism a first polynucleotide that encodes a first protein and a second polynucleotide that encodes a second protein, wherein expression of the second protein affects the post-translational modification of the first protein in cells of the organism and then isolating the modified protein from the organism.

Among preferred embodiments of this aspect of invention are those in which the polynucleotides are expressed in specific cells in the organism, those in which the first protein is secreted into a bodily fluid of the organism, particularly those in which the fluid is selected from the group consisting of blood, milk, urine or saliva. Also preferred in this aspect of the invention are embodiments in which the first polynucleotide encodes a precursor protein, the second polynucleotide enclode a protease and the precursor protein is processed by the protease in the cells.

Especially preferred in this aspect of the invention are those embodiments in which the cells are secretory cells of mammary glands and the first protein is secreted into milk of the organism. In this regard, embodiments in which the first polynucleotide encodes a precursor protein, the second polynucleotide encodes a protease, and the precursor protein is processed by the protease in the cells are highly preferred. Particular preferred are those embodiments in which the first protein is Factor VII, Factor VIII, Factor IX, prothrombin, Factor X, Protein C, Factor VII, Protein S, bone Gla protein, matrix Gla protein, growth arrest specific protein 6, antithrombin III, t-PA, erythropoietin, fibrinogen, immunoglobulin or albumin. Preferred proteases in this aspect of the invention include the paired basic amino acid cleaving enzymes. Especially highly preferred are embodiments in which the first polynucleotide encodes Protein C. Particularly highly preferred in this regard are embodiments in which the protease is PACE/furin.

Other preferred embodiments of this aspect of the invention include those in which a third polynucleotide encodes a third protein which affects protein gamma-carboxylation, the first protein requires gamma-carboxylation for maturation and the third protein affects gamma-carboxylation of the first protein in cells of the organism. In this regard, especially preferred are embodiments wherein the first polynucleotide encodes Protein C and the protease is PACE/furin.

In yet another aspect of the invention there is provided a product of a transgenic non-human multicellular organism, wherein the organism is characterized by having incorporated expressibly therein a first polynucleotide that encodes a first protein and a second polynucleotide that encodes a second protein, wherein expression of the second protein changes the post-translational modification of the first protein in cells of the organism and thereby changes the natural composition of a product made from the organism.

In certain preferred embodiments of this aspect of the invention the polynucleotides are expressed in specific cells in the organism. Also among preferred embodiments in which the second protein or the first and the second proteins are secreted into a bodily fluid of the organism, particularly blood, milk, urine or saliva. Especially highly preferred are embodiments wherein the product is milk or is derived from milk, the cells are secretory cells of mammary glands and the first, the second or both the first and the second proteins are secreted into and alter the milk of the organism. Embodiments wherein the first polynucleotide encodes a precursor protein, the second polynucleotide encodes a protease, and the precursor protein is processed by the protease in the cells also are highly preferred. Additionaly highly preferred embodiments are those in which the second protein is a protein that affects protein phosphoylation or a protease precursor protein, and the phosphorylation protein or the protease is secreted into and alters the composition of the milk.

In certain particularly preferred embodiments of this aspect of the invention the first protein is Factor VII, Factor VIII, Factor IX, prothrombin, Factor X, Protein C, Factor VII, Protein S, bone Gla protein, matrix Gla protein, growth arrest specific protein 6, antithrombin III, t-PA, erythropoietin, fibrinogen, immunoglobulin or albumin.

In certain especially preferred embodiments the protease is a paired basic amino acid cleaving enzyme.

In further preferred embodiments the first polynucleotide encodes Protein C.

Particularly preferred embodiments of this aspect of the invention are those in which the protease is PACE/furin.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
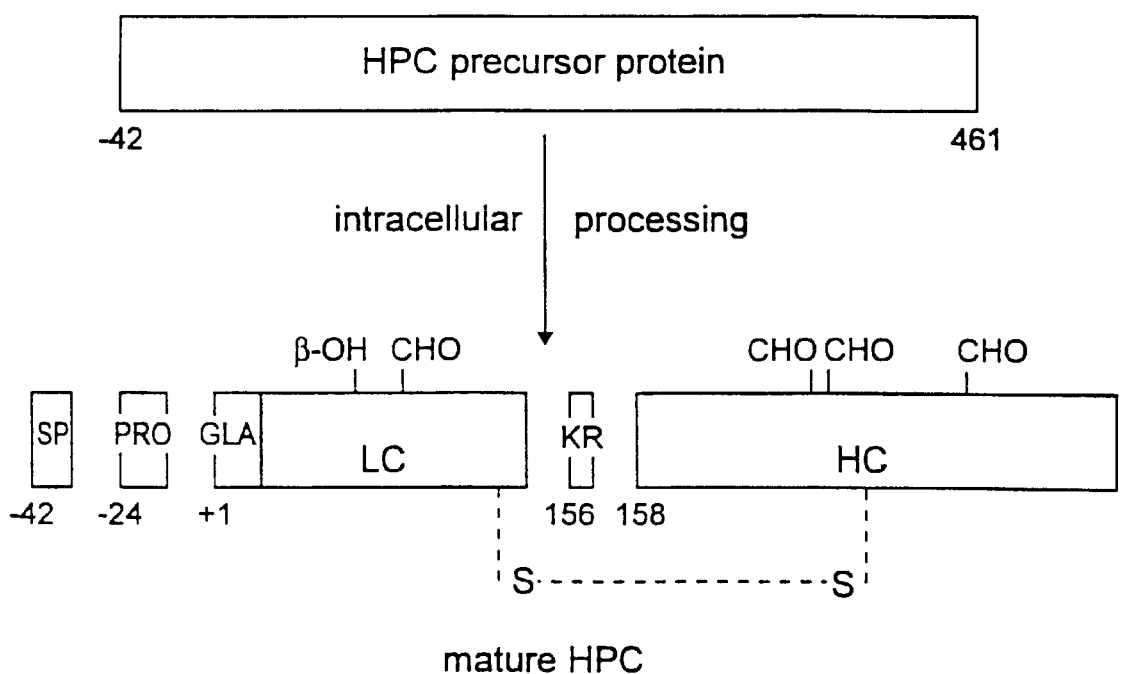
FIG. 1 is a schematic representation of the posttranslational modifications observed in human Protein C ("HPC"), showing that HPC initially is synthesized in hepatocytes as a single-chain 461 amino acid polypeptide, that following synthesis an 18-residue signal peptide ("SP") is removed, N-linked glycosides ("CHO") are added to $Asn^{97}$, $Asn^{248}$, $Asn^{313}$ and $Asn^{329}$, γ-carboxyl groups are added to nine amino-terminal proximal glutamic acid residues ("GLA") by vitamin K dependent gamma-carboxylase, the N-linked CHOs are further processed in the Golgi, a β-hydroxyl group ("β-OH") is added to $Asp^{71}$ and the 443 residue polypeptide is cleaved by a protease, releasing a 24-amino acid propeptide ("PRO") and a dipeptide $Lys^{156}$-$Arg^{157}$ ("KR"), and the correctly modified and processed HPC is secreted into the circulating plasma as a two chain protein composed of a light chain ("LC:1–155") and a heavy chain ("HC:158–420") linked by a disulfide bond.

The present invention relates to the expression of cloned genes to alter protein posttranslational modification and improve thereby the production of substances in transgenic non-human multicellular organisms.

In one particular aspect, the invention provides, surprisingly, that the posttranslational modification capacity of cells in non-human multicellular transgenic organisms can be altered without deleterious effect on the organisms.

Furthermore, the invention provides that the expression of enzymes that carry out posttranslational modifications can be used to alter not only posttranslational modification of proteins in cells of the organism, but also to alter, for instance, the composition of the cells, tissues, organs and physiological fluids of the organism and, in addition, the composition of products derived from the organisms.

In a particular aspect, the invention provides that expression of proteases can be used to alter the composition of milk and, thereby, of whey and other milk-components. Particularly in this regard, the invention can be used to alter the composition and properties of dairy products. Thus, the invention can be used not only to enhance production of substances in transgenic bioreactors, but also to increase the usefulness of products produced by the organism, such as dairy milk and milk-products such as that made from pigs, sheep and goats.

Also, the invention provides, surprisingly, that membrane proteins when expressed transgenically in mammary epithelial cells, are secreted into milk, are enzymatically active and can alter the composition of the milk in situ.

In a particular embodiment of the invention, DNA that encodes PACE/furin can be expressed in secretory cells of mammary glands of transgenic animals using a whey acid protein gene promoter ("WAP"). The PACE/furin expressed in the cells is secreted into milk; although, ordinarily it is a membrane-bound protein. Further, the secreted PACE/furin apparently reduces the amount of whey acid protein in the milk.

In addition, the invention provides co-expression of PACE/furin and human Protein C in secretory cells of the mammary glands of transgenic animals that not only brings about the aforementioned alterations of cells and milk, but also increases the amount of properly proteolytically processed Protein C in the milk.

In accordance with the invention, therefore, a gene is introduced into a non-human multicellular organism to alter protein posttranslational modification in cells of the organism. In a preferred embodiment, the gene expresses a protein that alters the composition of a protein, tissue or fluid in the organism. In the latter case, a particularly preferred embodiment of the invention involves a gene that expresses an enzyme in the mammary glands of a mammal, secretes the enzyme into milk and alters the composition of the milk.

In another preferred embodiment, two genes are introduced into an organism. The first gene encodes a first protein that undergoes posttranslational modification. The second gene encodes an enzyme that carries out a posttranslational modification of the first protein. In this embodiment, expression of the gene encoding the modifying enzyme alters maturation in the organism of the first protein encoded by the first gene.

In another preferred embodiment of the invention, production of a substance in a transgenic organism is improved by identifying a slow step of posttranslational modification that limits production of the protein in its desired form; and then augmenting the capacity of cells in the organism that produce the substance to carry out the modification so that it no longer is the limiting step. The same process may be reiterated two or more times to further optimize production until production is optimized.

In yet another preferred embodiment, the posttranslational modification is altered in specific cells or tissue in an organism. Also, the posttranslational modification may be inducibly altered in the cells in response to endogenous stimuli, such as hormones, or environmental variables, such a feed components.

In addition, in certain preferred embodiments, altered posttranslational mociciation affects maturation of protein in cells that secrete the protein into a bodily fluid, such as milk, urine, blood or saliva.

Posttranslational modifications, proteins for modification, methods and organisms of the invention are illustrated in the following generalized discussion. It will be appreciated that the discussion illustrates the scope of the invention, but does not, indeed cannot, describe each and every possible embodiment. Thus, the discussion is descriptive not limitative.

Illustrative Posttranslational Modifications

The posttranslational modification capacity of cells in a transgenic organism can be altered by expression of a transgene encoding an enzyme that modifies a protein. Many posttranslational modifications have been described and characterized. They have been the subject of many reviews, such as the reviews by F. Wold, *Posttranslational Protein Modifications: Perspectives and Prospects*, pp. 1–12 in POSTTRANSLATIONAL COVALENT MODIFICATION OF PROTEINS, B. C. Johnson, Ed., Academic, New York (1983); Seifter et al. *Analysis for protein modifications and nonprotein cofactors, Meth. Enzymol.* 182: 626–646 (1990); Rattan et al., *Protein synthesis, posttranslational modifications and aging*, in Ann. N.Y. Acad. Sci. 663: 48–62 (1992); Han et al., *Post-translational chemical modification(s) of proteins, Int. J. Biochem.* 24(1): 19–28 (1992); Han et al., *Post-translational chemical modifications of proteins—III, Int. J. Biochem.* 25(7); 957–970 (1994) and Han et al., *Int. J. Biochem.* 24(9): 1349–1363 (1994), all of which are incorporated by reference herein in their entireties.

The invention can be carried out for a variety of posttranslational modifications, in principle including any modification. Among the posttranslational modifications useful in the invention in this respect are acetylation, acylation, ADP-ribosylation, amidation, covalent attachment of a flavin, covalent attachment of a heme, covalent attachment of a nucleotide or a nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer RNA-mediated addition of amino acids to proteins such as arginylation, and ubiquitination, to name just some of the known posttranslational modifications of proteins that may be altered in accordance with the present invention.

The alteration of such posttranslational modifications of a protein in cells of a transgenic animal may be accomplished by changing the activity of proteins and enzymes that affect the occurrence of or efficiency with which a specific modification occurs, in selected transgenic cells or tissues in which the given protein is to be expressed.

Enzymes that catalyze many posttranslational modifications have been identified, purified and characterized, including enzymes that directly catalyze the modification, those that are involved in the metabolism and catabolism of the modification and those that affect the activity of a cell for the modification of a given protein. Genes that encode such enzymes can and, indeed, have been cloned, and expressed in cells of transgenic animals as described elsewhere herein.

The following list illustrates some of the enzymes that may be used in accordance with the present invention. Illustrative cDNAs and genomic clones encoding such enzymes also are set out below. It will be appreciated, however, that any given modification of a protein generally occurs as a result of the activities of a variety of enzymes and other proteins and substances in a cell. Thus, a modification of a protein in a cell of a transgenic animal may be affected, in accordance with the present invention, not only by transgenic expression of enzymes directly responsible for posttranslational modification, such as those illustrated below, but also by expression of proteins that act indirectly to affect such modifying enzymes, and thereby alter posttranslational modification of another protein expressed in the cells.

acetylation/deactylation

Posttranslational modification of proteins in cells by attaching or removing an acetyl group often is carried out by acetyltransferases and deacetylases; e.g., spermidine/spermine N1-acetyltransferase encoded by the "SSAT"

gene, and arylamine O-acetyltransferase, encoded by the NAT1 and NAT2 genes.

acylation

Acylation of proteins posttranslationally in cells often is carried out by acylesterases; e.g., rat proteolipid protein fatty acylesterase, rat myelin associated nonspecific esterase, *P.chrysogenum* acyl coA: 6-aminopanicillanic acid acyltransferase, encoded by the cloned penDE gene, and maize G3P acyltransferase, which has been cloned as a cDNA.

ADP-ribosylation

Illustrative of the enzymes that effectuate or alter post-translational ADP-ribosylation are mono (ADP-ribosyl) transferases A, C and D, poly (ADP-ribose) polymerase, which is encoded by the PARP gene, dinitrogen reductase activating glycohydrolase, human ADP-ribosylating factor, encoded by the ARF2 gene, and cholera toxin subunit A, encoded by the cholera toxin subunit A gene.

amidation

Among the enzymes that affect posttranslational amidation of proteins in cells is peptidylglycine α-amidating monooxygenase, encoded by the PAM gene, which has been cloned.

cross-linking

Enzymes involved in cross-linking reactions that occur in proteins posttranslationally in cells include cross-linking peroxidase and extensin.

disulfide bond formation

Enzymes of disulfide bond formation include, among others, disulfide oxidoreductases or isomerases; e.g., human protein disulfide isomerase, which has been cloned as a cDNA, rat protein disulfide isomerase, which also has been cloned as a cDNA, *E. coli* PDI-like protein, encoded by the dipz gene, *A. castellanii* PDI-like protein, which also has been cloned.

The formation of disulfide bonds in proteins within cells has been the subject of many reviews, such as Bardwell et al., *Cell* 74: 769–771 (1993) which is incorporated by reference herein in its entirety.

gamma-carboxylation

Enzymes which effectuate posttranslational gamma-carboxylation of proteins in cells include vitamin k-dependent carboxylases, for instance human and bovine glutamyl-carboxylase, which have been cloned as cDNAs. Posttranslational gamma-carboxylation also is affected by enzymes of vitamin K synthesis such as vitamin K epoxidases, vitamin K epoxide reductases, NADH- and dithiol-dependent vitamin K reductases. Gamma-carboxylation of proteins in cells has been the subject of much research and of numerous reviews, such as Furie et al., *Blood* 75(9) 1753–1762 (1990), which is incorporated by reference herein in its entirety.

glycosylation

The many enzymes that affect the glycosylation of proteins in cells include glycosyltransferases such as oligosaccaryl-, N-acetylglucoseaminyl-, fucosyl-, galactosyl- and sialyl-transferases, glucosidases and mannosidases, of which several cDNAs and genes cloned, including, for instance the gene for human α-fucosyltransferase. Post-translational glycosylation of proteins in cells has been the subject of many reviews, including, for instance, Goochee et al., *BIO/Technology* 9: 1348–1354 (1991) which is incorporated by reference herein in its entirety.

GPI anchor formation

Enzymes involved in forming glycosylphosphatidylinositol (GPI) anchors include GPI synthases, such as those encoded by the GPI synthase class A, F, H cDNAs, which have been cloned.

hydroxylation

Enzymes that affect posttranslational hydroxylation of proteins in cells include prolyl 4-hydroxylase, including human brain tryptophan hydroxylase, which has been cloned as cDNA, rabbit brain tryptophan hydroxylase, which also has been cloned as cDNA, human cholesterol 7 alpha-hydroxylase, which has been cloned as a cDNA, human tyrosine hydroxylase, the gene for which has been cloned, human phenylalanine hydroxylase, the gene for which also has been cloned, and lysyl hydroxylase.

iodination

Iodination of proteins in cells occurs primarily at tyrosine, and the enzymes that affect this posttranslational modification include thyroid peroxidase encoded by the thyroid peroxidase ("TPO") gene, which has been cloned.

lipid modification

A variety of lipidation and other lipid-related modifications occur posttranslationally in proteins in cells that may be used in accordance with the present invention. Some of these modifications are discussed individually elsewhere herein. Lipid modifications have been much studied and are described in a variety of reviews such as Chow et al., *Structure and biological effects of lipid modifications on proteins, Current opinion Cell Biol.* 4: 629–63 (1992) which is incorporated by reference herein in its entirety.

methylation and demethylation

Methylation commonly seen in proteins includes methylation of carboxyl-, N- and O- groups, carried out for instance, by protein methyltransferases, such as catechol O-methyltransferases, illustrated by the N-methyltransferase encoded by the *P. aeruginosa* gene pilD. Methylation also has been studied in detail and has been the subject of a variety of reviews, including, for instance, Clarke, S., *Protein Methylation, Current Opinion Cell Biol.* 5: 977–983 (1993). A review of methylation at carboxyl-terminal cysteine residues in particular is provided by Clarke, S., *Ann. Rev. Biochem.* 61: 355–386 (1992). Both of the foregoing references are incorporated by reference herein in their entirety.

oxidation

Posttranslational oxidation of proteins in cells is affected by, among others, lipid peroxidases, for example the lipid peroxidases of fatty acid oxidation.

proteolysis

A diverse array of proteases are known to carry out proteolytic events of protein maturation in cells. Specific proteolytic processing steps often are associated with transport across membranes and out of cell compartments, including excretion out of the cell. In addition, proteolytic cleavage often is required to activate proteins which initially are synthesized as inactive precursor polypeptides. The use of such enzymes is preferred in the invention. Particularly preferred are proteases that carry out cleavages of secretion or activation.

Enzymes involved in proteolytic posttranslational modification of proteins include, to name just an illustrative few, trypsin, chymotrypsin, *E.coli* signal peptidase, the metallo-carboxypeptidases such as carboxypeptidase B, the dipeptidyl aminopeptidases such as cysteine-, serine or aspartate proteases, including the human dipeptidyl peptidase IV encoded by the DPP4 gene and rat mitochondrial processing peptidase.

Proteolytic processing of proteins has been the object of prolonged and careful study and it has been reviewed extensively. One review, focusing on proteolytic processing particularly as it relates to physiological processes is Neurath, H, *Proteolytic processing and physiological regulation, TIBS* 14: 268–271 (1989), which is incorporated herein by reference in its entirety.

phosphorylation

Phosphorylation is a an important aspect of protein activity in cells and it is effectuated by a diversity of enzymes, including phosphorylases, kinases such as protein kinases A and C, including human TGF-6 receptor type II kinase which has been cloned as a cDNA, human protein phosphatase 1 (PP1) G-subunit, which also has been cloned as a cDNA, *A. thaliana* kinase-associated protein phosphatase ("KAPP") encoded by a cloned cDNA, *S. typhimurium* phosphatase encoded by the cobc gene.

prenylation

Prenylation of proteins posttranslationally in cells is carried out by, among others, prenyltransferases, including farnesyl-transferases and geranylgeranyl-transferases, illustrated by human heme A:farnesyltransferase which has been cloned as a cDNA, human CAAX farnesyltransferase which also has been cloned as a cDNA, yeast farnesyl-transferases encoded by the RAM1 and RAM2 genes, *E. coli* octaprenyl diphosphate synthase encoded by the ispB gene, beta subunit of *P. sativum* farnesyl-transferase which has been cloned as a cDNA, geranylgeranyl pyrophosphate synthase of *C. annum*, which also has been cloned as a cDNA. Protein prenylation is reviewed by, for instance, among others, Clarke S, *Ann. Rev. Biochem.* 61: 355–386 (1992), which focuses on isoprenylation of carboxyl-terminal cysteine residues, which is incorporated herein by reference in its entirety.

sulfation

Posttranslational sulfation of proteins in cells involves, for example, tyrosyl protein sulfotransferase ("TPST") and sulfate sulfatases, illustrated by human placental estrogen aryl sulfotransferase, and human brain estrogen aryl sulfotransferase, both of which have been cloned, and rat hepatic aryl sulfotransferase IV, which has been cloned. Sulfation of proteins is illustrated by the sulfation of Factor VIII. Posttranslational sulfation of tyrosine in proteins is reviewed by Niehrs et al., *Chemico-Biological Interactions*, 93: 257–271 (1994), which is incorporated by reference herein in its entirety.

ubiquitination

Isopeptide formation by the covalent attachment of ubiquitin is carried out by ubiquitin-conjugating isopeptidases, many of which are called E2s and are illustrated by at least ten identified yeast UBC genes and over 20 identified Arabidopsis UBC genes.

Ubiquitin activating enzymes also can be used in accordance with an aspect of the invention to affect posttranslational ubiquitination of proteins. Among these types of enzymes are the E1 enzymes that activate the α-carboxyl group of ubiquitin prior to isopeptide bond formation. Illustrative of enzymes of this type are those of the E1-encoding UBA1 gene of yeast and those of the three genes identified in Arabidopsis as E1-encoding genes. Also useful in this regard are enzymes of deubiquitination and substrate recognition factors involved in unbiquitination. The metabolism and role of ubiquitin and the ubiquitin protein degradation pathway are reviewed in M. Hochstrasser, *Current Opinion in Cell Biology* 4: 1024–1031 (1992), which is incorporated by reference herein in its entirety.

Posttranslational modifications often are specific to an amino acid, as noted in some places in the foregoing illustrative discussion. Thus, the posttranslational modification of specific amino acids in a protein can be selectively altered in cells of a transgenic organism by manipulating, in accordance with the present invention, the efficiency with which an amino acid-specific posttranslational modification is carried out in cells or tissues of an organism. The following list of known amino acid-specific posttranslational modifications of proteins illustrate this aspect of the invention. It will be appreciated that point mutations may be introduced into a given protein to avoid or engender one or more of these modifications at a specific amino acid residue in a protein.

amino terminus: formylation, acetylation, pyroglutamate formation, N-terminal arginylation, myristoylation.

arginine: N-methylation, ADP-ribosylation, phosphorylation.

asparagine: glycosylation, β-hydroxylation, deamidation, ADP-ribosylation.

aspartic acid: β-hydroxylation, β-carboxylation, phosphorylation, methylation, racemization (isomerization).

carboxy terminus: phosphatidylinositol derivatization, glycine-amidation.

cysteine: cystine formation, selenocysteine formation, heme linkage, myristoylation, prenylation, ADP-ribosylation, heme addition, palmitoylation, oxidation.

glutamic acid: γ-carboxyglutamate formation, C-methylation, ADP-ribosylation.

glutamine: deamidation, cross-linking, pyroglutamate formation.

histidine: methylation, diphthamide formation, phosphorylation, flavin addition.

lysine: N-acetylation, N-methylation, oxidation, hydroxylation, cross-linking, biotinylation, ubiquitination, hypusine formation.

methionine: selenomethionine formation.

phenylalanine: hydroxylation.

proline: hydroxylation, N-terminal methylation.

serine: phosphorylation, glycosylation, acetylation, phosphopantetheine addition.

threonine: phosphorylation, glycosylation.

tyrosine: iodination, phosphorylation, o-sulfation, flavin linkage, nucleotide linkage.

Any of the foregoing modifications may be altered in transgenic animals in accordance with the presently disclosed invention. Any of the foregoing enzymes, and genes that encode them, may be used in accordance with the invention herein disclosed to alter posttranslational modification of proteins expressed in transgenic organisms.

Illustrative Pproteins that may be Produced More Efficiently by Altering Posttranstional Modification of Cells in a Transgenic Organism The invention is applicable generally to any protein produced in cells or tissues of a transgenic organism. As noted above, the invention may be used to alter the efficiency of naturally occurring posttranslational modifications of a protein expressed in cells of a transgenic organism. It also may be utilized to manipulate posttranslational modification of a site introduced into a protein by point mutagenesis, or by more dramatic alteration of amino acid sequence of a protein.

Preferred embodiments of the invention in this regard relate to enzymes that perform posttranslational modifications of serum proteins, particularly the serum factors that play a role in hemostasis, blood clotting and the dissolution of blood clots. Especially preferred in this regard are the vitamin K-dependent proteins.

Among the proteins of particular interest in accordance with this aspect of the invention are Factor VII, Factor VIII, Factor IX, Factor X, Factor XIII, fibrinogen, prothrombin, plasminogen activators, such as t-PA, plasminogen, Protein S and Protein C, bone Gla protein, matrix Gla protein, growth arrest specific protein 6, antithrombin III, erythropoietin, immunoglobulins and albumin.

Particularly preferred alterations in the posttranslational modification of these proteins in transgenic organisms in accordance with the invention in this regard include enzymes for proteolytic processing, γ-carboxylation, β-hydroxylation, sulfation and glycosylation.

Especially preferred in this regard are enzymes for proteolytic processing, glycosylation, sulfation and γ-carboxylation. In some aspects of the invention, proteolytic processing particularly especially is preferred.

In this regard, enzymes of the PACE family are preferred, especially PACE/furin. PACE/furin is described, for instance, by Roebroek (1986) cited above. PACE/furin has been shown to process pro-von Willebrand factor, pro-nerve growth factor, proalbumin, and complement protein pro-C3, as described in Wise et al., *Proc. Nat'l Acad. Sci., U.S.A.* 87: 9378–9382 (1990), Van de Ven et al., *Mol. Biol. Rep.* 14: 265–275 (1990), Breshnahan et al., *J. Cell Biol.* 111: 2851–2859 (1990), Brennan et al., *J. Biol. Chem.* 266: 21504–21508 (1991) and Misumi et al., Biochem. *Biophys. Res. Comm.* 171: 3564–3568 (1990), which are incorporated by reference herein in their entirety. Moreover, PACE/furin, and PACE4 as well, likely also process a variety of other proteins, including growth factors, receptors, viral glycoproteins and coagulation factors, as indicated by their disseminated expression in many cell-types. Thus, PACE/furin may be expressed in cells of transgenic organisms to improve processing and maturation of these proteins, among others.

Notably, P1 and P4 arginine residues have been identified as amino acids important for efficient propeptide cleavage by PACE. For instance, see Derian et al., *J. Biol. Chem.* 264: 6615–6618 (1989), which is incorporated by reference herein in its entirety.

Guidance regarding expression constructs specifically in this regard is provided by Wasley (1993) and others, which report on genes encoding PAC enzymes expressed in cultured cells. The DNAs and cloning methods used to make PACE expression constructs for use in cultured cells can be adapted to the engineering of vectors for expression in transgenic organisms. It will be desirable, of course, to use promoters and other regulatory signals that will target expression of the PACE transgene to particular cells in an organism as described elsewhere herein. Illustrative Aspects of Constructs for Transgenic Expression using Routine Recombinant Dna Techniques DNAs for producing transgenic organisms can be obtained by conventional methods of recombinant DNA cloning. A general discussion of well known techniques for making suitable DNAs in this regard is provided by Maniatis et al., MOLECULAR CLONING, A LABORATORY MANUAL (Cold Spring Harbor Laboratory, 1982) and Sambrook et al., MOLECULAR CLONING, A LABORATORY MANUAL, Second Edition, Vol. 1–3 (Cold Spring Harbor Laboratory, 1989), which are incorporated by reference herein in pertinent part. Examples of DNA constructs that have been introduced into transgenic animals for systemic or tissue-specific expression are provided in GENETIC ENGINEERING OF ANIMALS, A. Puhler, Ed., VCH Verlagsgesellschaft, Weinheim, New York (1993), which also is incorporated by reference herein in pertinent part in this regard.

DNA coding for a given protein can be fused, in proper reading frame, with appropriate regulatory signals, as described in greater detail below, to produce a genetic construct which then may be amplified, for example, by propagation in a bacterial vector or by PCR, for subsequent introduction into a host organism, according to conventional practice.

Generally, the genes will be linked operatively to the cis-acting signals necessary for expression in a desired manner in an organism. Particularly preferred in this regard are promoters and other cis-acting regulatory elements that provide efficient expression in a particular cell-type. In the following discussion, the term promoter is used broadly and extends to cis-acting elements such as enhancers that may not always be considered in a strict technical sense, promoters.

The cis-acting regulatory regions useful in the invention include the promoter used to drive expression of the gene. Particularly useful in the invention are those promoters that are active specifically in given cell-types. In this regard, preferred promoters are active specifically in cells that secrete substances into bodily fluids. Especially useful in this regard are cells that can secrete substances into milk, urine, blood and saliva. Notably, therefore, cells of mammary gland, for instance, urinary tract, liver and salivary gland are especially useful.

Very particularly useful promoters in this regard in some aspects of the invention are active in mammary tissue. Particularly useful are promoters that are specifically active in mammary tissue, i.e., are more active in mammary tissue than in other tissues under physiological conditions where milk is synthesized. Most preferred in this regard are promoters that are both specific to and efficient in mammary tissue. By "efficient" is meant that the promoters are strong promoters in mammary tissue and support the synthesis of large amounts of protein for secretion into milk.

Among such promoters, the casein, the lactalbumin and the lactoglobulin promoters are preferred, including, but not limited to the α-, β- and γ-casein promoters and the α-lactalbumin and β-lactoglobulin promoters. Preferred among the promoters are those from rodents (e.g., mouse and rat), rabbits, pigs, sheep, goat, cow and horse, especially the rat β-casein promoter, the sheep β-lactoglobulin promoter and the rat and goat α-lactalbumin promoters.

The most preferred promoters are those that regulate a whey acidic protein (WAP) gene, and the most preferred WAP promoter is the murine WAP promoter. A most highly preferred promoter is the 4.2 kb Sau3A-Kpn1 promoter fragment of the mouse whey acidic protein promoter. It has been found that this fragment is highly effective in directing the production of high levels of a protein in the milk of a transgenic animal.

Among the sequences that regulate transcription that are useful in the invention, in addition to the promoter sequences discussed above, are enhancers (which may be considered part of the promoter), splice signals, transcription termination signals and polyadenylation signals, among others. Particularly useful regulatory sequences increase the efficiency of mammary cell specific expression of proteins in transgenic animals.

Especially useful in this regard are the other transcription regulatory sequences of genes expressed at high levels in mammary cells, such as the α-, β- and γ-casein genes and the α-lactalbumin and β-lactoglobulin genes mentioned above. Preferred sources for regulatory sequences in this regard are rodents (mice and rats), rabbits, pigs, sheep, goat, cow and horse. Exemplary of preferred regulatory sequences are those associated with the rat β-casein gene, the rat and goat α-lactalbumin genes and the sheep β-lactoglobulin gene, respectively.

Among the regulatory sequences most preferred for use in the present invention are those that encode hormone-induced milk proteins that are expressed only during pregnancy and lactation, such as those associated with whey acidic protein genes. Particularly preferred in this context are regulatory sequences of the murine whey acidic protein gene.

Among the sequences that regulate translation, in addition to the signal sequences discussed above, are ribosome binding sites and sequences that augment the stability of RNA. Especially useful are the translation regulatory sequences of genes expressed at high levels in mammary cells. For instance, the regulatory sequences of the α-, β- and γ-casein genes and the α-lactalbumin and β-lactoglobulin genes are preferred, especially those from rodents (mice and rats), rabbits, pigs sheep, goat cow and horse. Even more particularly preferred are the regulatory sequences of rat β-casein and the sheep β-lactoglobulin genes.

In another aspect, inducible promoters are preferred, particularly those that can be induced by environmental variables, such as food components. Notable in this regard are metallothionien promoters, which may be induced in animals by incorporating an appropriate metal inducer in feed. Metallothionien promoters have been used to express osteoglycin, epithelin, and bovine oncostatin M in transgenic animals, for instance, and Malik et al., *Molec. Cell. Biol.* 15: 2349–2358 (1995) provides a review of promoters that can be used for tissue-specific or inducible expression or both, and is incorporated by reference herein in its entirety. Also preferred are milk gene promoters which may be induced by lactogenic or steroid hormones.

Such promoters, useful in the invention for tissue-specific expression or inducible expression or both, include albumin promoters for liver-specific expression, $\alpha_1$-antitrypsin promoters for liver-specific expression, keratin-14 promoters for expression in epithelial cells and basal cells, RIβ promoters for expression especially in neurons, the insulin-1 promoters for expression in pancreatic β-cells, the LcK promoters for expression in thymocytes, the metal-induced metallothionien promoters and the hormone-induced milk protein gene promoters for expression in the mammary gland.

It will be appreciated that there may be additional regulatory elements that aid the production of transgenic organisms that express high levels of a protein. Some of these signals may be transcriptional regulators, or signals associated with transport out of the cell. Other signals may play a role in efficient chromosomal integration or stability of the integrated DNA.

Illustrative Organisms in which Posttranslational Modification may be Altered

Non-human multicellular organisms suitable for practicing the invention include plants and animals. Particularly preferred are mammals, other than humans, for producing substances in milk. All lactating animals, that is, all mammals, are suitable for use according to the present invention. Preferred mammals include mice, rats, hamsters, guinea pigs, rabbits, cats, dogs, pigs, sheep, goats, cows and horses. Livestock and research animals particularly are preferred. Among livestock, cows, goats, sheep and pigs are preferred, especially sheep and pigs. Among research animals are the foregoing and dogs, cats, hamsters, rabbits, rats and mice. Among these, hamsters, rats and mice are particularly preferred. Rats and mice are especially preferred in this regard.

Illustrative General Methods for Making Transgenic Organisms

Genes may be introduced into an organism in accordance with the invention using standard, well-known techniques for the production of transgenic organisms. These evolving techniques have been the subject of numerous reviews, including, for instance, TRANSGENESIS TECHNIQUES, Murphy et al., Eds., Human Press, Totowa, New Jersey (1993) and GENETIC ENGINEERING OF ANIMALS, A. Puhler, Ed., VCH Verlagsgesellschaft, Weinheim, New York (1993) which are incorporated by reference herein in their entirety.

For instance, DNA can be introduced into totipotent or pluripotent stem cells by microinjection, calcium phosphate mediated precipitation, liposome fusion, retroviral infection or by other means. Cells containing the heterologous DNA then can be introduced into cell embryos and incorporated therein to form transgenic organisms.

In a preferred method, developing cells or embryos can be infected with retroviral vectors and transgenic animals can be formed from the infected embryos.

In a highly preferred method, DNAs are microinjected into embryos, preferably at the single-cell stage, and the embryos are developed into mature transgenic animals.

Double and other multiply-transgenic animals can be made by introducing two or more different DNAs into the genomic DNA of a multi cellular organism using techniques described above. The DNAs may contain the same or different promoters and other expression-controlling signals. The cDNA or genomic DNAs encoding first and second proteins may be in separate or in a single construct. Furthermore, multiply-transgeinc organisms also can be made breeding. For instance, two singly-transgenic organisms can be crossed, using appropriate generally well known breeding techniques, to generate double-transgenic offspring having the transgenes of both the parents. Successive breeding can be used to introduce additional transgenecs, as well.

Cells, Tissues, Organs, Fluids and other Physiological Compartments for Expressing Transgenes Illustrative of the Invention Generally, any cell or tissue of an organism may be used in accordance with the present invention.

All-type specific expression that isolates altered posttranslational modifications to a particular physiological compartment is preferred in some aspects of the invention. By compartment is meant a physiologically and/or physically distinct aspect of an organism that localizes the alteration and insulates the organism as a whole from potentially undesirable systemic affects.

Preferred, in this regard, are cells and tissues that secrete substances into bodily fluids. In this regard, cells and tissues that secrete proteins into blood, saliva, urine and milk are highly preferred. Those that secrete proteins into urine or milk are very highly preferred. Among these, mammary epithelial cells that secrete proteins into milk are especially preferred. Also preferred are cells that secrete proteins into urine.

Illustrative Products of the Invention

It will be appreciated that the invention can be used to improve maturation of proteins in transgenic metazoic organisms. By altering maturation of proteins in cells of transgenic organisms the invention can be used to affect the production of substances in the organism. The production of substances can be directly affected by altering posttranslational modification or it can be indirectly affected. Thus, in the latter case, for instance, the invention can be used to alter the activity of an enzyme in a cell to influence the production of non-proteinaceous, as well as proteinaceous, products of cell metabolism and catabolism. For instance in this regard, the invention can be useful to alter phosphorylation of a protein posttranslationally and thereby alter its activity in converting a substrate to a product. In this way, altering posttranslational modification in accordance with the invention can be used to alter the production of any substance produced by cells in a transgenic organism.

More particularly, the invention can be used to alter protein maturation in a transgenic organism. For instance in this regard, the invention can be used to alter the posttranslational modification of milk proteins. In a particular example of this aspect of the invention, the phosphorylation and proteolytic processing of caseins in milk can be altered by means of the invention.

It will be appreciated that altered posttranslational modification of this type can be used, in a further aspect of the invention, to produce novel products in transgenic organisms. For instance, by means of the present invention the posttranslational modifications of caseins, known to play an important role in determining the qualities of milk and in making milk-derived products, may be altered. Thus, the aforementioned alteration of phosphorylation and proteolytic processing of caseins in milk can be used to produce transgenic mammals that provide novel milk, milk protein and milk products.

In addition, the present invention also can be used to produce the enzymes that carry out posttranslational modification, and to produce compositions, such as milk and milk-derived products, that contain the enzymes.

It will be appreciated in this regard, therefore, that the present invention can be applied generally to providing novel foods and food products.

An Illustration: Pace/Furin-Augemented Maturation of HPC in Transgenic Mouse Milk Vitamin K-dependent coagulation proteins represent one class of proteins that generally are synthesized as precursors and then undergo a series of proteolytic cleavages, among other events, that ultimately produce a fully matured protein. Proteases are responsible, in part, for maturation of precursor forms of coagulation proteins. Proteolytic processing of precursor forms of coagulation proteins are one type of posttranslational modification that can altered in transgenic organisms to improve production of a substance in accordance with the present invention. This aspect of the invention is exemplified by the expression of PACE/furin in mammary epithelial cells to increase production of mature HPC in milk of transgenic mice.

Efficient transgenic expression of vitamin K-dependent coagulation proteins with complete posttranslational modification and processing has remained a difficult challenge, despite some promising results. Similar obstacles have been observed for the expression of several of these proteins in a number of conventional cell lines.

For instance, it has been observed that HPC transfected cells in culture do not completely process the single chain of HPC. In fact, human liver cells apparently do not completely process single-chain to two-chain HPC in vivo. Observers have reported that the amount of precursor processed to the mature two-chain form was about 85–95% in the human liver, about 50% in liver-derived HepG2 cells, 30% in transfected baby hamster kidney cells and 80% in human kidney 293 cells. Chinese hamster ovary (CHO) and C127 mouse fibroblast cell lines not only did not process the protein to the mature form at all, but even secreted rHPC with the propeptide attached, as reported by Suttie, J. W., *Thromb. Res.* 44: 129–134 (1986) and Yan et al., *Trends in Biochemical Sci.* 14: 264–268 (1989).

rHPC secreted into the milk of transgenic animals was reported to be a mixture of pro- and single chain rHPC (Drohan et al., *Transgenic Res.* 3:355–364 (1994), and Velander et al., PNAS, U.S.A. 89:12003–12007 (1992) each of which is incorporated by reference herein in its entirety).

It has been suggested that varying inefficiency of the endoproteolytic maturation of rHPC in different cells may be due to saturation of the endogenous processing protease by rHPC production in the cells.

Expression of an appropriate protease might improve the endoproteolytic processing of rHPC in cells of a transgenic organism. Among the proteolytic processing enzymes mentioned above are the subtilisin-like serine proteases called prohormone convertases (PC) or paired basic amino acid cleaving enzymes ("PACE"). These proteins can be expressed in transgenic organisms in accordance with the invention to augment the proteolytic maturation of precursor forms of coagulation proteins.

As a first step in making transgenic mice with improved processing of HPC in mammary glands, DNAs were constructed in which cloned genes encoding HPC and PACE/furin were placed under expression control that directs expression of HPC and PACE/furin to mammary gland epithelia cells.

A preferred promoter for this purpose is the 4.2 kb Sau3A-Kpn1 fragment of the mouse whey acidic protein promoter. Other promoters and promoter fragments may be used to express proteins in mammary epithelial cells and other cells in like fashion.

In a preferred embodiment in this regard human genomic DNAs encoding Protein C are employed for expression of HPC. Among the most highly preferred human genomic DNAs is the fragment of the human Protein C gene beginning 21 basepairs upstream of the Protein C start codon and ending at the NheI site in the 3' end of the Protein C gene, which is 9.4 kb long and contains regulatory elements that engender high expression of human Protein C in milk. It will also be appreciated that the 9.4 kb Protein C fragment described is merely one highly preferred DNA in this regard. Of course, many other DNAs also may be employed in much the same way.

For expression of PACE/furin, any of a variety of PACE/furin DNAs that have been made and characterized can be employed. DNAs that encode PACE/furin and are suitable for use in this regard are described, for instance, in van de Ven et al., *Molecular Biology Reports* 14: 265–275 (1990) and Wasley et al., *J.Biol.Chem.* 268: 8458 (1993), which are incorporated by reference herein in their entirety.

A DNA containing a promoter is ligated to a DNA encoding Protein C and to a DNA encoding PACE/furin. The DNAs are arranged so that expression of the proteins is driven by transcription from the promoter. The ligation products can be inserted into an appropriate vector for propagation. Finally, DNA for injection is purified and used to produce transgenic mice. All of the techniques involved in these processes, which are described further above, and in references cited elsewhere herein, are well known and routinely practiced by those of skill in the art.

Pups developed from the injected embryos can be tested for the presence of the transgenes using standard techniques. For instance, the presence of transgenes in the animals can be determined by Polymerase Chain Reaction ("PCR") using primers specific for the injected PACE/furin and HPC DNAs in genomic DNA obtained from a small piece of tail tissue.

Likewise, expression of Protein C by lactating mice can be assayed using standard techniques, such as western blots, ELISAs, assays of procoagulant activity and the like described in the literature pertaining to transgenic expression of HPC, inter alia, as discussed elsewhere herein.

In particular, the Protein C contained in milk can be purified by known means without unduly affecting activity. One suitable approach to purification in this regard is immunoaffinity chromatography. Alternatively, the expressed Protein C can be isolated from the milk by other conventional means using methods described by, for instance, Drohan et al., pages 501–507 in ADVANCES IN BIOPROCESS ENGINEERING, Galindo et al. Eds., Kluwer Academic, Netherlands (1994), which is incorporated by reference herein in its entirety.

It is preferred that Protein C produced in milk pursuant to the present invention should be isolated as soon as possible after the milk is obtained from the transgenic mammal, thereby mitigating any deleterious effect(s) on the stability of the protein.

The degree of proteolytic maturation of the expressed Protein C can be assessed by separating the whey proteins from whole milk, resolving the proteins by size by SDS/PAGE and blotting the proteins onto a filter and probing the filter with an antibody that recognizes all forms of HPC to visualize rHPC in the milk.

rHPC in milk from nontransgenic mice, mice transgenic for HPC, and mice transgenic for HPC and PACE/furin can be compared side-by-side in blots to assess directly the effect of PACE/furin expression on conversion of recombinant preproHPC to proHPC, proHPC to mature rHPC, and single-chain rHPC to two-chain rHPC. The observed forms of rHPC can be sequenced to determine if PACE/furin-mediated cleavage sites correspond to the sites of natural processing. Activity assay also can be applied to assess the fidelity of rHPC produced in transgenic mice with natural HPC.

The foregoing is illustrated in yet more detail in the specific examples below. It will be appreciated that the illustrations are not limitative and that the same paradigm can be used to alter posttranslational processing of any protein in accordance with the invention.

Thus, for instance, other enzymes that can properly cleave rHPC in cells in a transgenic animal can be used in the same way as PACE/furin, and other proteins can be expressed and their processing augmented in transgenic animals in the same way that proteolytic maturation of HPC is augmented above.

The present invention is further described by reference to the following illustrative examples.

As a demonstration that the processing of complex heterologous proteins in organs of transgenic animals can be improved, a DNA encoding human PACE/furin has been expressed in mammary gland cells of transgenic mice to increase the production of properly processed two-chain HPC and to alter the composition of mouse milk and mouse whey.

EXAMPLE 1
Construction of WAP/HPC and WAP/PACE DNAs and Generation of HPC and HPC/PACE Double-Transgenic Mice Mice transgenic for an intact HPC gene and either (i) an intact PACE cDNA or (ii) a mutated PACE cDNA encoding an enzymatically inactive protein ("PACEM") were produced using standard methods by co-injecting constructs containing the two cDNAs into mouse embryos.

Figure 2:
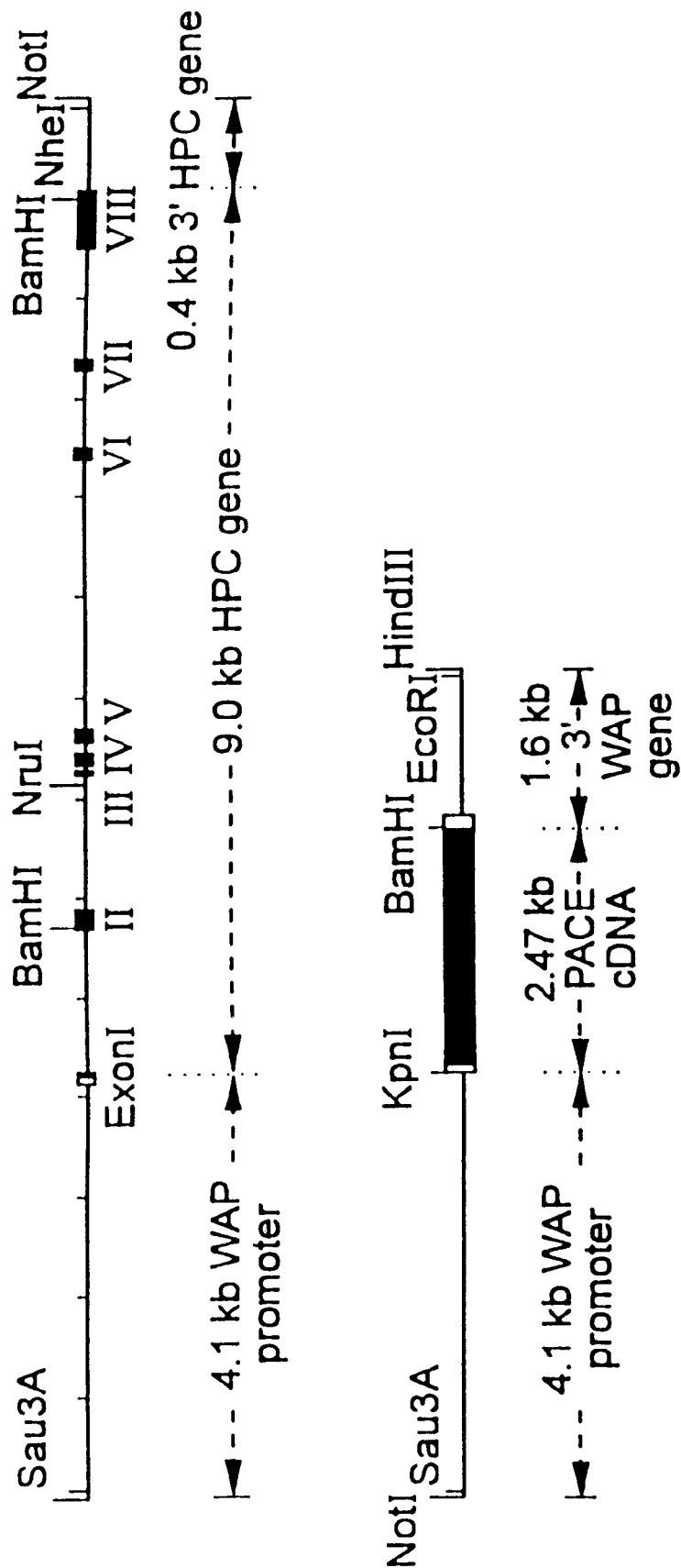
FIG. 2 is a schematic representation of illustrative mWAP/HPC and mWAP/PACE constructs of the examples. Exons are depicted by solid boxes, untranslated mWAP exon sequences by closed boxes, 5'- and 3' flanking and intron sequences by lines. The sequence of the junction between the mWAP promoter and PACE cDNA is GGTACCaCAC-CATG (SEQ ID NO:3). The 3' junction between the PACE cDNA and the mWAP gene has the sequence TTTATCTGggGGATCCC (SEQ ID NO:2). The mWAP sequence is in bold letters, the linker sequence is in small letters and the PACE sequence is in italics. Both constructs contain identical 5'-flanking mWAP sequences from position –4098 to position +25.

The posttranslational processing of human Protein C is shown diagramatically in FIG. 1. Illustrative DNA constructs of the present examples are depicted schematically in FIG. 2.

To target expression of PACE and PACEM to mammary glands, the cDNAs were placed under expression control of a mouse WAP promoter. The promoter is well known and has been used to direct expression and secretion of rHPC into milk in transgenic mammals, as described in, for instance, U.S. Pat. No. 5,589,604, Drohan et al., *Transgenic Res.* 3: 355–364 (1994) and Paleyanda et al., *Transgenic Res.* 3: 335–343 (1994) each of which is incorporated by reference herein in its entirety.

Intronless WAP/PACE cDNAs were used to express low amounts of PACE. Several groups have documented the inefficient expression of intronless transgenes in the mammary gland (Whitelaw et al., *Transgenic Res.* 1: 3–13 (1991) and Hennighausen, L., *Protein Expr. and Purif.* 1: 3–8 (1990) each of which is incorporated by reference herein in its entirety.

The WAP/HPC DNA construct comprised a 4.1 kb mouse whey acidic protein (WAP) promoter (33) and a 9 kb HPC gene with 0.4 kb 3' nontranslated sequences. It was constructed from readily available DNAs using well-known techniques, (29) as described in Drohan et al., *Transgenic Res.* 3: 355–364 (1994) and Hogan et al., MANIPULATING THE MOUSE EMBRYO, Cold Spring Harbor Press (1986), each of which is incorporated by reference herein in its entirety.

To make WAP/PACE and WAP/PACEM, a 4.1 kb Sau3A-KpnI WAP promoter fragment, and BamHI-EcoRI fragment containing 1.6 kb of 3' WAP nontranslated sequences were cloned into pUC19; generating plasmid pHL215. A 2.47 kb EcoRI-SalI fragment, comprising the 794-codon human PACE coding sequence and 74 bases of 3' untranslated sequence, was excised from a PACE cDNA clone (Wise et al., *Proc. Nat'l Acad. Sci., USA* 87: 9378–9382 (1990)) and treated with Mung bean nuclease. PACE or mutated PACE Ser$^{261}$ to Ala ("PACEM"), fragments then were inserted into SmaI-digested pHL215 plasmids in which PACE or PACEM cDNA is under expression control of the WAP promoter, generating plasmids pHL252 and pHL255, respectively.

WAP/PACE and WAP/PACEM DNAs for injection were released from the plasmid by NotI-HindIII digestion, and then purified for microinjection.

Transgenic mice were generated by coinjecting WAP/HPC and WAP/PACE fragments in a 2:1 molar ratio, at a total concentration of 2 μg/ml. PCR was used to detect the transgene DNAs in tail DNA from mice produced from the injected embryos. Transgenic mice were identified by HPC and PACE-specific PCR products in DNA from tail samples. Primers that define a 502 bp region at the 5' end of the HPC gene and a 216 bp region of the mouse WAP gene were used as probes for the WAP/HPC DNA (Drohan et al., *Transgenic Res.* 3: 355–364 (1994). Primers that define a 260 bp region at the 5' end of the PACE cDNA were used as probes for PACE DNA (see Wise et al., Proc. Natil. Acad. Sci., U.S.A. 87:9378–9382 (1990), which is incorporated by reference herein in its entirety).

Four founders carrying both HPC and PACE transgenes were detected among thirteen mice screened. All four HPC/PACE founders transmitted the transgenes to their offspring. The male, C1.2, showed high transgene transmission frequency. The three females, C2.2, C4.1 and C5.2, showed low transmission frequencies and appeared to be mosaic. Two founders carrying both the HPC and PACEM transgenes and one founder carrying the PACE transgene alone were detected among seven mice screened. One double-transgenic founder, M2.3, transmitted both PACEM and HPC transgenes to offspring. Lines were established from the five founders that exhibited transmission to progeny and mice from these lines were employed in further studies.

EXAMPLE 2
Detection of PACE and WAP Expression by Northern Blotting

Total RNA was prepared from tissues of transgenic females of the F1 or F2 generations and from control mice using standard techniques. RNA was isolated from fresh or frozen tissues in a single step procedure using acid guanidinium thiocyanate phenol-chloroform extraction (available commercially, for instance, as RNAzol, Molecular Research Center, Inc. and described in Chomczynski et al., *Anal. Biochem.* 162: 156–159 (1987) which is incorporated herein by reference in its entirety). The RNA was analyzed on Northern blots using 15 µg of total RNA for each sample. RNA from two animals or more was analyzed in each experiment. The sample RNAs were separated under denaturing conditions on formaldehyde-1.2% agarose gels and then transferred by downward alkaline blotting for 2.5 h onto nylon membranes (available, for instance, as GENE-SCREEN PLUS DuPont NEN) as described in Chomczynski, P., *Anal. Biochem.* 201: 134–139 (1992), which is incorporated by reference herein in its entirety.

The membranes were screened with probes specific for HPC, PACE and 18S rRNA. A 0.5 kb BamHI-NheI fragment from the HPC 3' region of HPC was used as a probe for PACE mRNA. A 0.85 kb BamHI-SalI fragment from the PACE cDNA was used as a probe for PACE MRNA. A 0.75 kb BamHI-SphI fragment of the 18S ribosomal RNA (rRNA) gene in pN29111 (ATCC No. 63178) was used as a probe for 18S rRNA. An intact 2.5 kb human PACE cDNA fragment was used as a probe for the endogenous murine PACE mRNA. The probes were labeled with $^{32}p$ by random primer polymerization labelling.

Filters were prehybridized for 0.5 h at 68° C. using an accelerated hybridizing solution (such as QUIK-HYB from Stratagene). They then were hybridized for 2 h at 68° C. in a buffer containing 0.5 to 1.0 ng/ml denatured probes and sonicated salmon sperm DNA.

After hybridization, the filters were rinsed twice in 2×SSC, 0.1% SDS for 15 minutes at room temperature, then washed once in 0.1×SSC, 0.1% SDS for 30 min at 60° C. and thereafter autoradiographed.

Northern hybridization of replicate blots with the three probes revealed that both the HPC and PACE transgenes were expressed in the lactating mammary glands of HPC/PACE mice.

The major species of HPC mRNA was approximately 1725–1775 nucleotides (nt) in length, with a distinct minor species approximately 200 nucleotides shorter. The shorter MRNA may have been produced by an alternative 3' polyadenylation site (29). Several HPC precursor RNAs of about 2250, 2400 and 4800 nucleotides also were detected.

Human PACE mRNA of the expected size, 2700 nucleotides, was detected by the PACE cDNA probe. Endogenous mouse PACE transcripts were not detected, even upon prolonged exposure of autoradiograms. However, upon hybridization under conditions of lower stringency, endogenous transcripts were detected at levels at least one order of magnitude lower than the transgene mRNA.

The amount of rHPC secreted into the milk of founder and later generation mice was determined by a sandwich ELISA, using HPC-specific polyclonal antibodies, as described in EXAMPLE 3 and Table 1 below.

EXAMPLE 3
Detection of Matured rHPC in Milk of Transgenic Animals

Mice were administered 0.3 ml (0.6 IU) of oxytocin i.p. to facilitate collection of milk. Milk samples were collected between days 7 and 15 of lactation. The milk was diluted with 2 volumes of phosphate-buffered saline, pH 7.4, containing 50 mM EDTA, centrifuged twice at 15,000 rpm for 15 min at 4° C., and stored at −80° C. before use. EDTA was used to solubilize casein micelles, and improve recovery of micelle-associated rHPC.

The concentration of rHPC in the milk was measured by sandwich ELISA (enzyme linked immunosorbent assay). Sheep anti-HPC polyclonal antibody immobilized in microtiter wells was used to capture rHPC in the diluted milk samples (Drohan et al., *Transgenic Res.* 3: 355–364 (1994)). A rabbit anti-HPC antibody was used to detect captured rHPC bound to the immobilized antibody. Horseradish peroxidase (HRP) conjugated to a goat anti-rabbit IgG antibody then was bound to the immobilized rabbit anti-HPC antibody. Bound Peroxidase was detected by activity assay using a calorimetric substrate, 3,3',5,5'-tetramethylbenzidine (TMB). Substrate utilization was measured by the change in absorbance at 650 nm during 10 minutes. Purified plasma-derived HPC diluted in control milk served as a standard.

Results from these experiments are shown in Table 1, below.

TABLE 1 rHPC in milk of HPC/PACE transgenic mice
Milk was collected between days 7 and 15 of lactation and the concentration of rHPC in defatted milk was assayed by ELISA, as described herein. Six to eight different milk samples were analyzed from each HPC/PACE line. Each sample was analyzed in duplicate. (Except "*" indicates value from ELISA of a single milk sample.)

| MOUSE LINE | $F_0$ GENERATION rHPC (mg/ml) | $F_{1-3}$ GENERATIONS rHPC (mg/ml) |
|---|---|---|
| C1.2 | — | 0.451–0.896 |
| C 2.2 | 0.020* | 0.308–1.626 |
| C 4.1 | 0.004–0.075 | 0.908–1.352 |
| C 5.2 | 0.001–0.004 | 0.734–1.154 |
| M 2.3 | — | 0.169–0.331 |
| 6.4 | 0.512–0.706 | 0.190–0.532 |

The level of rHPC detected in the milk of the founder generation HPC/PACE mice was significantly lower than in the milk of mice from later generations, which ranged from 0.45 to 1.63 mg/ml. This may reflect mosaicism of the founder mice. Lower amounts of rHPC were detected in the milk of HPC mice from the 6.4 line and in HPC/PACEM mice.

Coexpression of rHPC and PACE in the mammary gland did not result in deleterious effects on the health of the females over successive lactations. Similar to normal non-transgenic mice from HPC/PACE lines C2.2, C5.2, as well as HPC/PACEM transgenic mice were able to raise litters of 10–15 pups, indicating that PACE did not affect nursing capabilities even at expression levels an order of magnitude higher than the endogenous gene. Animals from HPC/PACE lines C1.2 and C4.1 reared only 2–6 of their pups, although their health remained unaffected.

EXAMPLE 4
Western Blot Analysis of HPC in Transgenic Milk shows that Maturation is Augmented by Co-Expression of PACE/Furin Milk proteins were separated under reducing conditions on 10% SDS-polyacrylamide gels alongside prestained molecular weight markers. Following electrophoresis, the gels were silver stained or transferred to nitrocellulose membranes (such as HYBOND-ECL from Amersham).

The blots were reacted serially with (i) the 8861 anti-HPC monoclonal antibody that recognizes an epitope on the activation peptide of the heavy chain or a sheep anti-HPC polyclonal antibody, and then with (ii) HRP-conjugated secondary antibodies. After binding the HRP conjugates and washing the filters, the activity of bound HRP was determined using enhanced chemiluminescence. Scanning densitometry of the developed Western blots was employed to quantitate the proteins.

The analysis showed that rHPC from the milk of HPC or HPC/PACEM transgenic mice consisted of approximately 40–60% rHPC single chain form, which is more than the 5–15% present in human plasma. In sharp contrast, the amount of single chain form in the milk of HPC/PACE double-transgenic mice expressing PACE averaged less than 5%, indicating efficient conversion of the precursor to the mature two-chain form by the transgenic expression of the heterologous PACE gene.

EXAMPLE 5
Purification and Amino Acid Analysis of rHPC from Milk of Transgenic Mice Shows that Co-Expression of PACE/Furin Increases Correct Maturation Pooled whole milk, 1.5–2 ml, from several F2 and F3 animals of the C5.2 line was thawed, diluted with 20 ml of 50 mM Tris, 0.15 M NaCl, 2 mM EDTA, 2 mM benzamidine, pH 7.2 and centrifuged at 30,000 g for 15 min at 4° C. The spun aqueous phase was filtered through a 0.45 μm membrane (for instance, MILLEX-HA from Millipore). The filtrate was loaded at a linear flow rate of 17 cm/hr onto a 1.5 cm×2.7 cm column consisting of 8861 MAb immobilized on Sepharose CL-4B resin (from Pharmacia) equilibrated with 50 mM Tris, 0.15 M NaCl, 2 mM EDTA, 2 mM benzamidine, pH 7.2. The loaded column was washed with 5 mM ammonium acetate, pH 5.0 and then bound rHPC was eluted in 0.5 M ammonium acetate, pH 3.0, immediately neutralized with 3 M Tris and stored at −80° C.

The recovery of rHPC from milk was more than 80%. Electrophoretic analysis of rHPC purified from the milk of HPC/PACE mice as described above, revealed that rHPC polypeptides migrated slightly faster than plasma-derived HPC. The difference probably was due to differences in glycosylation (Drohan et al., *Transgenic Res.* 3: 355–364 (1994)).

Some single-chain rHPC was removed from rHPC obtained from HPC mice by the previously described purification process, but the amount of single-chain rHPC in rHPC purified from HPC/PACE mice was substantially lower (Drohan et al., *Transgenic Res.* 3: 355–364 (1994). Furthermore, no other rHPC-specific lower molecular weight bands were observed upon nonreducing and reducing SDS-PAGE. Amino acid sequence analysis of rHPC from the milk of HPC/PACE mice revealed two amino terminal sequences, beginning at positions 1 and 158 of HPC, as shown in Table 2, below.

$Ala^1$ has previously been identified as the site of removal of the HPC propeptide (Foster et al., *Proc. Nat'l Acad. Sci., USA* 82: 4673–4677 (1985)). $Asp^{158}$ is the site of cleavage of the internal $Lys^{156}$-$Arg^{157}$ dipeptide during conversion of the HPC zymogen to mature, two-chain HPC.

TABLE 2

Amino-Terminal sequence of Transgenic rHPC
Purified rHPC was subjected to automated Edman degradation and the sequence compared to that of rHPC from HPC transgenic mice. Numbering indicates the first amino acid of the propeptide (-24), of the light chain (+1) and of the heavy chain of mature HPC (+158). (γ) represents non-detected residues corresponding to γ-carboxyglutamic acid residues present in the HPC sequence.

| CHAIN | COMPOSITION | PERCENT |
|---|---|---|
| HPC from Human Plasma | | |
| Light chain +1 | A N S F L γ γ L R H S S L γ R γ C (SEQ ID NO:3) | 100 |
| Heavy chain +158 | D T E D Q E D Q V D P R L I D G K (SEQ ID NO:4) | 100 |
| rHPC from HPC Transgenic Mice | | |
| Pro-peptide -24 | T P A P L D S V F S S S (SEQ ID NO:5) | 20–30 |
| Light Chain +1 | A N S F L E E L R H S S L E R E C (SEQ ID NO:6) | 70–80 |
| Heavy chain +158 | D T E D Q E D Q V D P R L I D G K (SEQ ID NO:4) | 100 |
| rHPC from HPC/PACE Transgenic Mice | | |
| Light chain +1 | A N S F L E E L R H S S L E R E (SEQ ID NO:7) | 100 |
| Heavy chain +158 | D T E D Q E D Q V D P R L I D G K (SEQ ID NO:4) | 100 |

The results show that processing of both the propeptide and the single chain of the Protein C precursor occurs at the appropriate sites in mammary cells in HPC/PACE mice. In contrast, 20–30% of the rHPC secreted into milk contains the propeptide in HPC transgenic mice (Drohan et al., *Transgenic Res.* 3: 355–364 (1994)).

Furthermore, the good yields of Glu residues at positions 6, 7, 14, 16, 19, 20, 25, 26 and 29 in the light chain indirectly indicate that γ-carboxylation of glutamic acid residues is inefficient at these expression levels, consistent with earlier observations (Drohan et al., *Transgenic Res.* 3: 355–364 (1994)).

EXAMPLE 6
Expression of PACE/Furin Decreases Whey Acid Protein Content of Milk of Transgenic Animals Western blot analysis of mouse whey acid protein ("WAP") in milk proteins from control non-transgenic mice, mice transgenic for HPC, mice doubly transgenic for HPC and PACEM and mice doubly transgenic for HPC and PACE showed that HPC/PACE expression decreased the WAP content of milk.

Milk proteins were analyzed by western blots essentially as described above. Briefly, defatted milk proteins were separated by electrophoresis through 14% SDS-PAGE gels. The separated proteins were transferred onto filters by standard western blotting procedures and then WAP was visualized on the filters using an anti-WAP antibody. Whey proteins from non-transgenic (i.e., normal mice), HPC/PACE transgenic mice, HPC transgenic mice, and HPC/PACEM transgenic mice were analyzed side-by-side. The amount of WAP protein in milk from non-transgenic, HPC and HPC/PACEM mice was roughly the same in all cases, while the amount of WAP protein HPC/PACE transgenic mice decreased by about 40–60%.

EXAMPLE 7
PACE/Furin is Secreted into Milk of Transgenic Animals

The presence of PACE/furin was analyzed in milk of transgenic mice using the western blotting techniques described herein above. Whey proteins from the milk of control and transgenic mice and separated by PAGE in 8% SDS-polyacrylamide gels. The gels were blotted onto filters and PACE was visualized using a PACE/furin-specific antibody. A band of approximately 50 kD that appeared in all of the samples apparently was due to artefactual non-specific binding of the secondary antibody. No furin-specific band was seen in milk from non-transgenic control mice, HPC or HPC/PACEM transgenic mice. A PACE/furin-specific band of approximately 80 kDa was detected in milk proteins from HPC/PACE transgenic mice.

EXAMPLE 8
PACE/Furin is an Active Protease in Milk of Transgenic Animals

PACE/furin activity was determined in milk from control and HPC/PACE transgenic animals by monitoring conversion of single-chain rHPC to two-chain rHPC, as follows.

Whole milk from mice was incubated at 37° C. for 0, 1 and 3 hours, defatted by centrifugation and proteins from each sample were resolved by SDS-PAGE in 8–16% gels. In addition, milk from HPC/PACE mice was mixed with milk from HPC mice in a 1:10 ratio to detect activity of secreted PACE/furin in the milk of the HPC/PACE mice. The gels were blotted onto filters and HPC was visualized by western blotting techniques using an HPC-specific antibody, as described herein above.

Samples containing milk from HPC/PACE mice contained less single-chain HPC than milk from the other mice. Activity of the secreted PACE/furin was indicated by the decrease in precursor.

---

What is claimed is:

1. A non-human transgenic mammal which produces a post-translationally modified first protein, wherein said mammal comprises somatic and germ cells having stably incorporated into the genome of said cells, a first exogenous polynucleotide encoding a first protein susceptible to modification by PACE/furin and a second exogenous polynucleotide encoding PACE/furin, each of said first and second exogenous polynucleotides operatively linked to a mammary epithelial cell specific promoter, and wherein said mammal expresses said first exogenous polynucleotide and said second exogenous polynucleotide in the mammary gland epithelial cells, wherein said PACE/furin post-translationally modifies said first protein, such that said modification results in a post-translationally modified first protein.

2. The non-human transgenic mammal according to claim 1, wherein said post-translational modification is required for maturation of said first protein.

3. The non-human transgenic mammal according to claim 1, wherein said first polynucleotide encodes a precursor protein and said precursor protein is modified by said PACE/furin.

4. The non-human transgenic mammal according to claim 3, wherein said first protein is Factor VII, Factor VIII, Factor IX, prothrombin, Factor X, Protein C, Protein S, bone Gla protein, matrix Gla protein, growth arrest specific protein 6, antithrombin III, t-PA, erythropoietin, fibrinogen, immunoglobulin or albumin.

5. The non-human transgenic mammal according to claim 1, wherein said first protein is a vitamin-K dependent protein.

6. The non-human transgenic mammal according to claim 1, wherein said first protein is Factor VII, Factor VIII, Factor IX, prothrombin, Factor X, Protein C, Protein S, bone Gla protein, matrix Gla protein, growth arrest specific protein 6, antithrombin III, t-PA, erythropoietin, fibrinogen, immunoglobutin or albumin.

7. The non-human transgenic mammal according to claim 1, wherein said first polynucleotide encodes Protein C.

8. The non-human transgenic mammal according to claim 1, wherein said first protein is Factor VIII.

9. The non-human transgenic mammal according to claim 1, wherein said first protein is Factor IX.

10. The non-human transgenic mammal according to claim 1, wherein said first protein is fibrinogen.

11. The non-human transgenic mammal according to claim 1, further comprising a third exogenous polynucleotide operatively linked to a mammary epithelial cell specific promoter that encodes a third protein, which gamma-carboxylates said first protein.

12. The non-human transgenic mammal according to claim 11, wherein said first polynucleotide encodes Protein C.

13. The transgenic non-human mammal according to claim 1, wherein said mammal is selected from the group consisting of mice, rats, hamster, guinea pigs, rabbits, pigs, sheep, goats and cows.

14. A method for producing a post-translationally modified first protein in a non-human transgenic mammal, wherein said mammal comprises somatic and germ cells having stably incorporated into the genome of said cells, a first exogenous polynucleotide encoding a first protein susceptible to modification by PACE/furin and a second exogenous polynucleotide encoding PACE/furin, each of said first and second exogenous polynucleotides operatively linked to a mammary epithelial cell specific promoter, wherein said method comprises expressing said first exogenous polynucleotide and said second exogenous polynucleotide in the mammary gland eptithelial cells, and wherein said PACE/furin post-translationally modifies said first protein, such that said modification results in a post-translationally modified first protein, and obtaining said post-translationally modified first protein from the milk of said mammal.

15. The method according to claim 14, wherein said post-translational modification is required for maturation of said first protein.

16. The method according to claim 14, wherein said first polynucleotide encodes a precursor protein and said precursor protein is modified by said PACE/furin.

17. The method according to claim 14, wherein said post-translationally modified first protein is secreted by said mammary gland epithelial cells into milk of said mammal.

18. The method according to claim 14, wherein at least one of said first protein or said PACE/furin is secreted into said milk of said mammal.

19. The method according to claim 14, wherein said first protein is a vitamin-K dependent protein.

20. The method according to claim 14, wherein said first protein is Factor VII, Factor VIII, Factor IX, prothrombin, Factor X, Protein C, Protein S, bone Gla protein, matrix Gla protein, growth arrest specific protein 6, antithrombin III, t-PA, erythropoietin, fibrinogen, immunoglobulin or albumin.

21. The method according to claim 14, wherein said first polynucleotide encodes Protein C.

22. The method according to claim 14, wherein said first protein is Factor VIII.

23. The method according to claim 14, wherein said first protein is Factor IX.

24. The method according to claim 14, wherein said first protein is fibrinogen.

25. The method according to claim 14, further comprising a third exogenous polynucleotide operatively linked to a mammary epithelial cell specific promoter that encodes a third protein, which gamma-carboxylates said first protein.

26. The method according to claim 25, wherein said first polynucleotide encodes Protein C.

27. The method according to claim 14, wherein said mammal is selected from the group consisting of mice, rats, hamster, guinea pigs, rabbits, pigs, sheep, goats and cows.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:1:

GGTACCACAC CATG                                                              14

(2) INFORMATION FOR SEQ ID NO:2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:2:

TTTATCTGGG GGATCCC                                                       17

(2) INFORMATION FOR SEQ ID NO:3:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO:3:

```
Ala Asn Ser Phe Leu Xaa Xaa Leu Arg His Ser Ser Leu Xaa Arg Xaa
1               5                   10                  15

Cys
```

(2) INFORMATION FOR SEQ ID NO:4:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO:4:

```
Asp Thr Glu Asp Gln Glu Asp Gln Val Asp Pro Arg Leu Ile Asp Gly
1               5                   10                  15

Lys
```

(2) INFORMATION FOR SEQ ID NO:5:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:5:

```
Thr Pro Ala Pro Leu Asp Ser Val Phe Ser Ser Ser
1               5                   10
```

(2) INFORMATION FOR SEQ ID NO:6:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO:6:

```
Ala Asn Ser Phe Leu Glu Glu Leu Arg His Ser Ser Leu Glu Arg Glu
1               5                   10                  15

Cys
```

(2) INFORMATION FOR SEQ ID NO:7:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:7:

```
Ala Asn Ser Phe Leu Glu Glu Leu Arg His Ser Ser Leu Glu Arg Glu
1               5                   10                  15
```